United States Patent
Nabel et al.

(10) Patent No.: US 7,414,035 B2
(45) Date of Patent: Aug. 19, 2008

(54) HKIS COMPOSITION AND METHODS OF USE

(75) Inventors: Gary J Nabel, Washington, DC (US); Elizabeth G. Nabel, Washington, DC (US); Manfred Boehm, Potomac, MD (US)

(73) Assignee: The Regents of the University of Michigan, Ann Arbor, MI (US)

( * ) Notice: Subject to any disclaimer, the term of this patent is extended or adjusted under 35 U.S.C. 154(b) by 306 days.

(21) Appl. No.: 11/128,063

(22) Filed: May 12, 2005

(65) Prior Publication Data

US 2005/0203050 A1  Sep. 15, 2005

Related U.S. Application Data

(60) Continuation of application No. 10/798,532, filed on Mar. 11, 2004, now Pat. No. 6,894,154, which is a division of application No. 09/378,517, filed on Aug. 20, 1999, now Pat. No. 6,770,473.

(60) Provisional application No. 60/097,710, filed on Aug. 21, 1998.

(51) Int. Cl.
  *A61K 31/70* (2006.01)
  *A61K 39/23* (2006.01)
  *C12N 15/00* (2006.01)
  *A61F 2/06* (2006.01)

(52) U.S. Cl. .............. 514/44; 424/450; 424/233.1; 435/320.1; 623/1.11; 604/508; 536/23.5

(58) Field of Classification Search ............ None
See application file for complete search history.

(56) References Cited

U.S. PATENT DOCUMENTS 5,674,192 A * 10/1997 Sahatjian et al. ............. 604/28
5,985,635 A   11/1999 Bandman et al. ........... 435/194
6,391,632 B1 * 5/2002 Dubensky et al. ........... 435/325

FOREIGN PATENT DOCUMENTS

WO   WO 95/10623   4/1995

OTHER PUBLICATIONS

Li et al (J. Biol. Chem. 277(13), 11352-11361, 2002).*
Miller et al. (FASEB J. 9: 190-199, 1995).*
Deonarain (Exp. Opin. Ther. Patents 8(1):53-69, 1998).*
Verma et al (Nature 389: 239-242, 1997).*
Crystal (Science 270:404-410, 1995).*
Pouton et al (Adv. Drug Del. Rev. 46: 187-203, 2001).*
Read et al (Adv. Gen. 53:19-46, 2005).*
Anderson (Nature 392:25-30, 1998).*
Romano et al (Stem Cells 18: 19-39, 2000).*
Somia and Verma (Nature Reviews Genetics 1: 91-99, 2000).*
Rosenberg et al, Science 287:1751, 2000.*
Juengst (BMJ 326: 1410, 2003).*
Maucuer et al (J. Biol. Chem. 272(37): 23151-13156, 1997).*
Chen et al (J. Clin. Invest. 99(10): 2334-2341, May 1999).*
Morisaki et al (Biochem. Biophys. Res. Comm. 240: 386-390, 1997).*
Wu et al (Canc. Res. 61: 7325-7332, 2001).*
Olive et al (Gene 151(1-2): 81-88, 1994).*
Mahairas, G.G., EST database: Accession # AQ024916, submitted Jun. 1998.
Orkin et al., Report and Recommendations of the Panel to Assess the NIH Investment in Research on Gene Therapy, www.nih.gov Dec. 1995.
Verma, M. et al., Gene Therapy: Promises, Problems and Prospects, Nature, vol. 389, Sep. 1997, pp. 239-242.
Eck, S. L. et al., 1996, Ch 5. Gene Based Therapy, Goodman & Gillman's The Pharmacological Basis of Therapeutics. pp. 77-101.
Mahairas, G.G. et al., HS_2183_A2-B07_MF CIT Approved Human Genomic Sperm Library D Homo Sapiens Genomic Clone, database sheet, XP-002125938, Jun. 23, 1998.
Hiller, K. et al., Soars Total Fetus Nb2HF8 9w Homo Sapiens cDNA Clone, database sheet, XP-002125939, Jun. 11, 1997.
Hiller, K. et al., Soars Total Fetus Nb2HF8 9w Homo Sapiens cDNA Clone, database sheet, XP-002125940, Jun. 11, 1997.
Maucuer, A. et al., KIS is a Protein Kinase with and RNA Recognition Motif, The Journal of Biol. Chem., vol. 272, No. 37, Sep. 12, 1997, pp. 23151-23156.
Muller, D. et al., Cdk2-dependent phosphorylation of p27 facilitates its Myc-induced release from cyclin E/cdk2 complexes, Oncogene, 15, pp. 2561-2576, 1997.
Sheaff, R. et al., Cyclin E-CDK2 is a regulator of $p27^{Kip}$, Genes and Development, 11, pp. 1464-1478, 1997.
Polyak, K. et al., Cloning of $p27^{Kip}$, a Cyclin-Dependent Kinase Inhibitor and a Potential Mediator of Extracellular Antimitogenic Signals, Cell. vol. 87, pp. 59-66, Jul. 15, 1994.
PCT International Search Report for PCT/US99/18903.
Boehm, M. et al., A Growth Factor-Dependent Nuclear Kinase Phosphorylates $p27^{Kip}$ and Regulates Cell Cycle Progression, The EMBO Journal, vol. 21, No. 13, pp. 3390-3401, 2002.

* cited by examiner

*Primary Examiner*—Richard Schnizer
(74) *Attorney, Agent, or Firm*—Brinks Hofer Gilson & Lione

(57) ABSTRACT

Disclosed herein are novel composition and methods for altering the proliferation of a cell. Included are wild-type and mutant hKIS polypeptides along with cyclin kinase inhibitors containing mutations that prevent their inhibition with serine/threonine kinases.

17 Claims, 1 Drawing Sheet

HKIS COMPOSITION AND METHODS OF USE

RELATED APPLICATIONS

This non-provisional application is a continuation of and incorporates by reference in its entirety U.S. patent application Ser. No. 10/798,532, filed Mar. 11, 2004 now U.S. Pat. No. 6,894,154, which is, of division of and incorporates by reference in its entirety U.S. patent application Ser. No. 09/378,517, filed Aug. 20, 1999 now U.S. Pat. No. 6,770,473, which claims priority to and incorporates by reference in its entirety U.S. Provisional Application Ser. No. 60/097,710, filed Aug. 21, 1998.

BACKGROUND OF THE INVENTION

It is known that transitions between phases of the cell cycle are catalyzed by a family of cyclin-dependent kinases (Nurs, 1990; Hartwell et al, 1974). In many cells, transit through G1 of the cell cycle and entry into S phase requires a binding and activation of cyclin/cyclin-dependent kinase complexes (CDK), predominantly cyclin D-cdk4,6 and cyclin E-cdk2 (Sherr, 1994; Sherr, 1996).

The cyclin-dependent kinase inhibitors (CKIs) are naturally-occurring gene products which inhibit cyclin-CDK activity and phosphorylation of retinoblastoma protein (Rb), resulting in G1/S growth arrest (D. O. Morgan, 1995; Sherr and Roberts, 1995). CKIs directly implicated in CDK regulation are $p21^{cip1/Waf1}$ (Xiong et al., 1993; Harper et al., 1993), $p27^{Kip1}$ (Pyoshima and Hunter, 1994; Polyak et al., 1994; Coats et al., 1996), and $p16/p15^{INK4}$ (Serrano et al., 1993).

The ability of CKIs to arrest cells in G1 have made the proteins of particular use in gene therapy techniques for treating diseases or disorders associated with cell proliferation, such as cancer and leukemias, psoriasis, bone diseases, fibroproliferative disorders, atherosclerosis, restenosis, and chronic inflammation. However, very little is known about the regulation of these very important proteins in vivo.

BRIEF SUMMARY OF THE INVENTION

The inventors have discovered a novel mechanism of regulation of CKIs. Specifically, disclosed herein are serine/threonine kinases that inhibit the ability of CKIs to arrest cells in G1. In light of this discovery, the inventors were able to construct a transdominant mutant of a serine/threonine kinase that interferes with the respective endogenous serine/threonine kinase when introduced into a cell transgenically. Furthermore, the inventors were able to construct a CKI unable to be inhibited by a serine/threonine kinase. Such constructs may be used alone, together, or in conjunction with other therapies for inhibiting or reducing cell proliferation.

Thus, the present invention provides isolated nucleic acid segments. Such isolated nucleic acid segments may encode wild-type or mutant hKIS polypeptides. In preferred embodiments, the isolated nucleic acid segments encode a transdominant mutant hKIS. A transdominant mutant hKIS is a polypeptide that is capable of interfering with the ability of endogenous hKIS to phosphorylate p27. Thus, a transdominant mutant hKIS would lead to or enhance cell cycle arrest in a cell containing the mutant. An example of a transdominant mutant hKIS is an hKIS that contains a mutation altering its serine/threonine kinase activity, such as that encoded by SEQ ID NO:3).

In other embodiments of the present invention, the isolated nucleic acid encodes a cyclin kinase inhibitor containing a mutation at a serine or threonine amino acid. It is preferred that the cyclin kinase inhibitor retains its ability to arrest the cell cycle. Examples of mutated cyclin dependent kinases include mutated of p16, p21, p27, and p57.

The isolated nucleic acids of the present invention may be contained in an expression vector. The expression vector may be a plasmid or a viral vector. The viral vector may be replication deficient and includes a retroviral vector, an adenoviral vector, an adenovirus associated viral vector, or a lentiviral vector.

Furthermore, the isolated nucleic acids of the present invention may be contained in or associated with a medical device, such as a catheter.

The isolated nucleic acids or polypeptides of the present invention may be included in a kit, such kits may also include one or more medical devices for administering the nucleic acid or polypeptide to a patient or one or more cells of a patient.

DETAILED DESCRIPTION OF THE INVENTION

Figure 1:
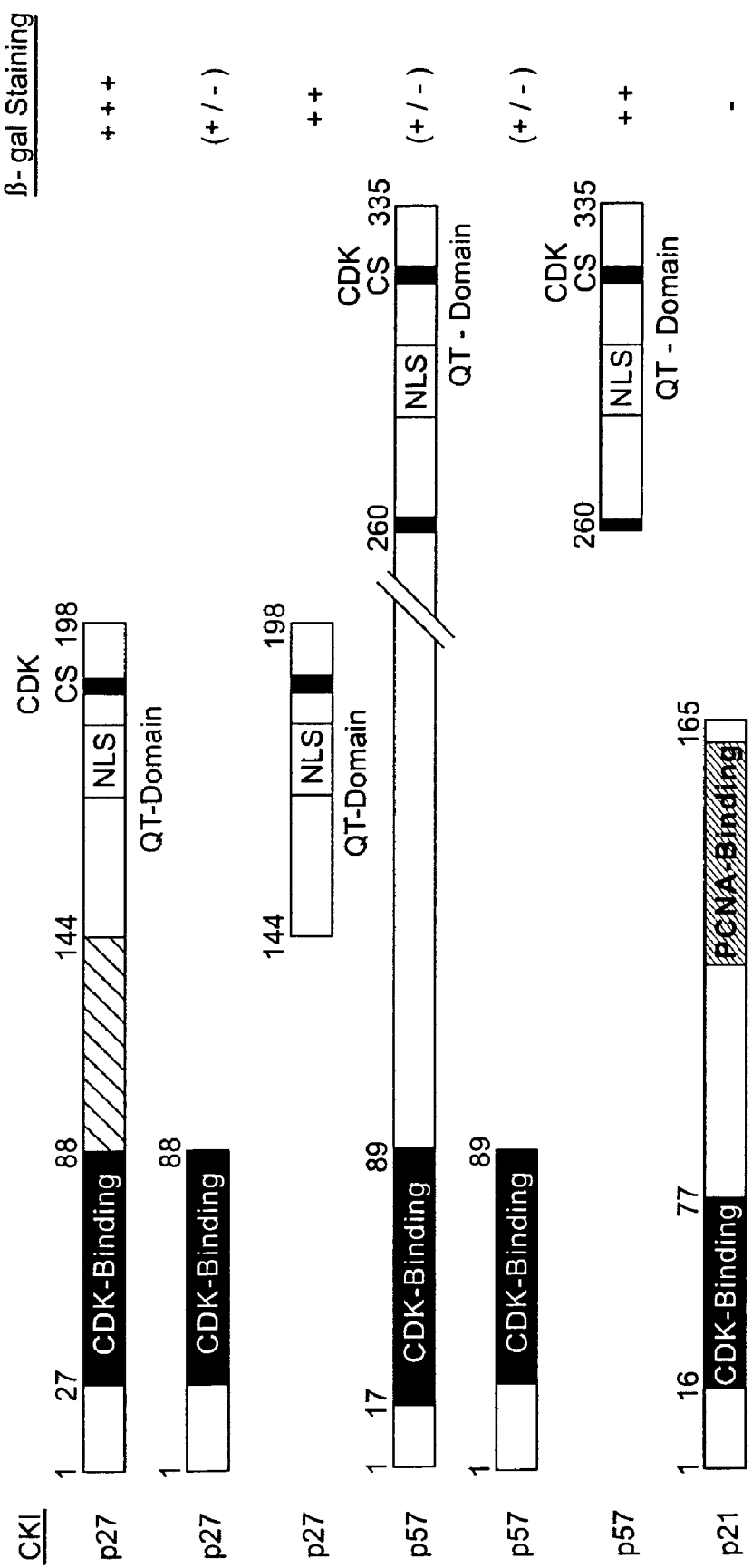
FIG. 1. hKIS interacts with the QT domain of $p27^{Kip1}$ in *Saccharomyces cervisiae*. hKIS was identified using a yeast two hybrid assay (Example 1). hKIS was co-transfected with either $p27^{Kip1}$, $p27^{Kip1}$ (1-85aa), $p27^{Kip1}$ (144-198aa), $p57^{Kip2}$, $p57^{Kip2}$ (1-87aa), $p57^{Kip2}$ (260-335aa), and $p21^{Cip1}$ into yeast β-galactosidase assay (Sherr, 1994) on selection plates was performed, and the intensity was categorized by visualization at the intensity of the staining. CKI=cyclin-dependent kinase inhibitor; β-gal=β-galactosidase; CDK CS=cyclin-dependent kinase consensus sequence; NLS=nuclear localization signal; PCNA=proliferating cell nuclear antigen; +++=very strong staining; ++=strong staining; (+/−)=weak staining; −=no staining. No staining was observed with the GBT9 backbone or irrelevant negative controls, pLAM5' (human laminC/GAL4 DNA binding domain) or pVA3 (murine p53/GAL4 DNA binding domain) (Clontech, Palo Alto, Calif.).

In order to identify proteins that bind to p27, the inventors first utilized the yeast two-hybrid system to identify proteins that associate with p27 in vivo (Fields and Song, 1989; Chien et al., 1991; Durfee et al., 1993; Harper et al., 1993). Such analyses led to the discovery a novel gene that encodes a polypeptide that binds to p27 in the yeast assay. This gene is included herein as hKIS (human KIS) DNA and protein sequences (SEQ ID NO:1 and SEQ ID NO:2, respectively).

Although the sequence of the hKIS gene is 92% identical to a rat KIS sequence that has been reported (Maucuer et al., 1997; GenBank Acc. No. X98374)), its potential role in p27 binding and/or as part of the cell cycle pathway(s) has not previously been suggested.

It is well established that certain dominant genes promote tumorigenesis or cell proliferation by binding and reducing the activity of tumor suppressor proteins. Prominent examples include MDM2, which binds and inhibits the tumor suppressor function of p53, and the transforming proteins encoded by certain DNA viruses (e.g., the SV40 large T antigen), that also bind and inactivate tumor suppressors such as p53 and Rb. The inventors have determined that the interaction between hKIS and p27 reduces the ability of p27 to arrest cells in G1.

The gene encoding hKIS serves as a dominant gene controlling cell proliferation. Thus, inhibiting hKIS is a therapeutic approach. hKIS inhibition could be achieved by providing to a hyperproliferative cell, or administering to a patient, any compound that inhibits the hKIS gene, mRNA, or protein.

Thus, embodiments of the present invention include assays to find compounds capable of reducing the level of transcription of the hKIS gene. Such assays include contacting a cell with a compound and comparing the amount of hKIS RNA in the cell as compared to a control. This comparison may be done through any of a number of techniques including, Northern blotting, semi-quantitative PCR, or RNase protection assays. Preferred compounds are hKIS antisense oligonucleotides.

Other embodiments of the present invention include assays to find compounds that inhibit the ability of serine/threonine kinases, such as hKIS, to phosphorylate CKIs, such as p27. Such methods may be in vitro or in vivo. For example, the assay may include contacting a cell or protein composition comprising a hKIS and p27 protein with a compound and determine the ability of the two proteins to interact with each other. The ability of the two proteins to interact may be determined by a number of methods including immunoprecipitation, plasmon resonance techniques, or fluorescence energy transfer techniques. In some instances the substance may permit binding of the two proteins but inhibit phosphorylation. Such instances may be determined by detecting phosphorylation of the CKI.

In some embodiments, cell proliferation may be inhibited by providing to a hyperproliferative cell, or administering to a patient, a CKI comprising one or more mutations that prevent or reduce phosphorylation of the CKI's serine/threonine residues by a serine/kinase, such as hKIS. A such mutated CKI would maintain the ability to arrest cells in G1 phase, as shown in example 1, yet not be inhibited by the expression of a serine/threonine kinase. The mutation may prevent interaction of the CKI with the respective serine/threonine or prevent phosphoryation of one or more serine/threonine subsequent to interaction of the two proteins. In a preferred embodiment, the mutated CKI is p27 comprising a serine to alanine mutation at amino acid number 10.

Other methods of inhibiting cell proliferation are described herein and include, but are not limited to, compounds that reduce transcription of the endogenous hKIS, compounds that prevent translation of hKIS mRNA, compounds that prevent the interaction of hKIS and p27, and compounds that prevent phosphorylation of p27 by hKIS.

Genes and DNA Segments

Important aspects of the present invention concern isolated DNA segments and recombinant vectors encoding wild-type, polymorphic or mutant hKIS, and the creation and use of recombinant host cells that express wild-type, polymorphic or mutant hKIS, using the sequence of SEQ ID NO:1.

The present invention concerns DNA segments, isolatable from mammalian and human cells, that are free from total genomic DNA and that are capable of expressing a protein or polypeptide that has p27-binding activity. In preferred embodiments, the DNA segments encode hKIS.

As used herein, the term "DNA segment" refers to a DNA molecule that has been isolated free of total genomic DNA of a particular species. Therefore, a DNA segment encoding hKIS refers to a DNA segment that contains wild-type, polymorphic or mutant hKIS coding sequences yet is isolated away from, or purified free from, total mammalian or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified wild-type, polymorphic or mutant hKIS gene refers to a DNA segment including wild-type, polymorphic or mutant hKIS coding sequences and, in certain aspects, regulatory sequences, isolated substantially away from other naturally occurring genes or protein encoding sequences. In this respect, the term "gene" is used for simplicity to refer to a functional protein, polypeptide, or peptide encoding unit. As will be understood by those in the art, this functional term includes both genomic sequences, cDNA sequences and smaller engineered gene segments that express, or may be adapted to express, proteins, polypeptides, domains, peptides, fusion proteins and mutants.

"Isolated substantially away form other coding sequences" means that the gene of interest, in this case the wild-type, polymorphic or mutant hKIS gene forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a wild-type, polymorphic or mutant hKIS protein or peptide that includes within its amino acid sequence a contiguous amino acid sequence in accordance with, or essentially as set forth in, SEQ ID NO:2 corresponding to wild-type, polymorphic or mutant human KIS. Moreover, in other particular embodiments, the invention concerns isolated DNA segments and recombinant vectors that encode a hKIS protein or peptide that includes within its amino acid sequence the substantially full length protein sequence of SEQ ID NO:2.

The term "a sequence essentially as set forth in SEQ ID NO:2" means that the sequence substantially corresponds to a portion of SEQ ID NO:2 and has relatively few amino acids that are not identical to, or a biologically functional equivalent of, the amino acids of SEQ ID NO:2.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 will be sequences that are "essentially as set forth in SEQ ID NO:2", provided the biological activity of the protein is maintained.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1, is used in the same sense as described above and means that the nucleic acid sequence substantially corresponds to a portion of SEQ ID NO:1 and has relatively few codons that are not identical, or functionally equivalent, to the codons of SEQ ID NO:1. DNA segments that encode proteins exhibiting p27-binding activity will be most preferred.

The term "functionally equivalent codon" is used herein to refer to codons that encode the same amino acid, such as the six codons for arginine or serine, and also refers to codons that encode biologically equivalent amino acids (see Table 1, below).

TABLE 1

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 79%; or more preferably, between about 80% and about 89%; or even more preferably, between about 90%, 92%, 93%, 94% and about 99%; of nucleotides that are identical to the nucleotides of SEQ ID NO:1 will be sequences that are "essentially set forth in SEQ ID NO:1."

Sequences that are essentially the same as those set forth in SEQ ID NO:1 may also be functionally defined as sequences that are capable of hybridizing to a nucleic acid segment containing the complement of SEQ ID NO:1 under relatively stringent conditions. Suitable relatively stringent hybridization conditions will be well known to those of skill in the art, as disclosed herein.

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementarily rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein.

The nuclear acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may very considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a short contiguous stretch identical to or complementary to SEQ ID NO:1, such as about 8, about 10 to about 14, or about 15 to about 20 nucleotides. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 10, 11, 12, 13, 14, 15, 16, 17, 18, 19, 20, etc.; 21, 22, 23, etc.; 30, 31, 32, etc.; 50, 51, 52, 53, etc.; 60, 61, 62, 63, 64, etc.; 100, 101, 102, 103, etc.; 150, 151, 152, 153, etc.; including all integers through the 200-500; 500-1000; 1,000-2,000 ranges.

The various probes and primers designed around the disclosed nucleotide sequences of the present invention may be of any length. By assigning numeric values to a sequence, for example, the first residue is 1, the second residue is 2, etc., an algorithm defining all primers can be proposed;

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It will also be understood that this invention is not limited to the particular nucleic acid and amino acid sequences of SEQ ID NO:1. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins or peptides that have variant amino acids sequences.

The DNA segments of the present invention encompass biologically functional equivalent hKIS proteins and peptides. Such sequences may arise as a consequence of codon redundancy and functional equivalency that are known to occur naturally with nucleic acid sequences and the proteins thus encoded. Alternatively, functionally proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to disrupt the kinase properties of hKIS or to alter the domain of hKIS responsible for interaction with p27.

One may also prepare fusion proteins and peptides, e.g. where the hKIS coding regions are aligned within the same expression unit with other proteins or peptides having desired functions, such as for purification or immunodetection purposes (e.g., proteins that may be purified by affinity chromatography and enzyme label coding regions, respectively).

Encompassed by the invention are DNA segments encoding relatively small peptides, such as, for example, peptides of from about 15 to about 50 amino acids in lengths, and more preferably, of from about 15 to about 30 amino acids in length; and also larger polypeptides up to and including proteins corresponding to the full-length sequences set forth in SEQ ID NO:2. It is contemplated that such DNA segments encoding polypeptides or mutants thereof may be useful in methods of interring with the biological function of the endogenous hKIS protein. In a preferred embodiment, the DNA segment is that of SEQ ID NO: 3.

In other aspects, the present invention concerns isolated DNA segments and recombinant vectors encoding mutant CKIs and the creation and use of recombinant host cells that express mutant CKIs. CKIs have the ability to arrest the cell cycle and are useful in therapies designed to inhibit or otherwise limit cell proliferation. Examples of cell proliferation disorders that can be affected by the modified CKIs described herein include restenosis, atherosclerosis, cancer, smooth muscle cell proliferative diseases or disorders of any vessel in the body, and the like. Examples of CKI include p16, p21, p27, p57. The present invention includes a DNA segment encoding a CKI modified such that it containing a mutation of one or more serine or threonine residues. Such mutants maintain the ability to arrest cells under going proliferation and are no longer able to be phosphorylated/inhibited by a serine/threonine kinase. In preferred embodiments, the serine or threonine residue is changed to alanine. However, it is contemplated that the serine or threonine may be changed to essentially any other amino acid as long as the change allows the CKI protein to maintain its functional activity and is no longer phosporylatable/inhibited by a serine/threonine kinase. Alanine generally is preferred because it tends to have the least amount of effect on the conformation or function of the protein possessing the mutation. Other amino acids, such as glycine, also can be used to advantage.

The serine and threonine residues available for modification to a non-phophorylatable residue, such as alanine, are provided in Table 2. In light of the present disclosure, one of ordinary skill in the art readily could construct a nucleic acid construct with a mutation at one or more serine or threonine codons, express the nucleic acid, and test the activity of the encoded protein. One or more nucleotides of a serine or threonine codon can be modified to create an alanine codon. The codons for alanine are listed in table 1. One of ordinary skill in the art would be able to create the mutation and test for a decrease in the ability of the CKI to be phosphorylated/inhibited by a serine/threonine kinase and maintain its ability to arrest the cell cycle. Methods of testing the ability of a CKI to inhibit the cell cycle is described herein (Example 1).

In one embodiment, the serine or threonine residue/codon to be modified occurs within residues 1-20 of the encoded protein. In another embodiment the serine/threonine residue to modified occurs within residues 1-15 or 1-10 of the encoded protein. In other embodiments, p16 is modified at S4 or T10; p21 is modified at S2 or S15; p27 is modified at S2, S7, S10, or S12; p57 is modified at S2, S5, S8, T9, S10 or T11.

TABLE 2

| CKI Protein | GenPept Acc. No. | Serine/Threonine Residues |
|---|---|---|
| p16 | AAB60645.1 | S4, T10, S35, S48, T69, T71, T85, T129, S132, S144 |
| p21 | AAB29246.1 | S2, S15, S27, S31, T55, T57, T80, S98, T105, S114, S116, T118, S123, S130, S137, T145, S146, T148, S153, S160 |
| p27 | AAA20240.1 | S2, S7, S10, S12, S27, T42, S56, S83, S106, S110, S112, S125, T128, T135, S138, S140, T142, T157, S160, S161, T162, T170, S175, S178, S183, T187, T198 |
| p57 | AAA85095.1 | S2, S5, S8, T9, S10, T11, T20, T27, S28, S32, S43, T80, S84, S86, T94, S116, S125, S138, S146, T147, S223, S244, S247, T254, S258, S268, S273, S282, S287, S288, S297, S299, S306, T310 |

Recombinant Vectors, Host Cells and Expression

Recombinant vectors form important further aspects of the present invention. The term "expression vector or construct" means any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

Particularly useful vectors are contemplated to be those vectors in which the coding portion of the DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene.

The promoter may be in the form of the promoter that is naturally associated with the expressed gene, as may be obtained by isolating the 5' non-coding sequences located upstream of the coding segment or exon, for example, using recombinant cloning and/or PCR technology, in connection with the compositions disclosed herein (PCR technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with the gene in its natural environment. Such promoters may include promoters normally associated with other genes, and/or promoters isolated from any other bacterial, viral, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include a human or viral promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 3 and 4 below list several elements/promoters which may be employed, in the context of the present invention, to regulate the expression of a heterologous gene. This list is not intended to be exhaustive of all the possible elements involved in the promotion of transgene expression but, merely, to be exemplary thereof.

Any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial and viral promoters if the appropriate bacterial or viral polymerase is provided, either as part of the delivery complex or as an additional genetic expression construct.

TABLE 3

Promoter and Enhancer Elements

| Promoter/Enhancer | References |
|---|---|
| Immunoglobin Heavy Chain | Banerji et al., 1983; Gilles et al., Grosschedl and Baltimore, 1985; Atchinson and Perry, 1986, 1987; Imler et al., 1987; Weinberger et al., 1984; Kiledjian et al., 1988; Porton et al; 1990 |
| Immunoglobin Light Chain | Queen and Baltimore, 1983; Picard and Schaffner, 1984 |
| T-Cell Receptor | Luria et al., 1987; Winoto and Baltimore, 1989; Redondo et al.,; 1990 |

TABLE 3-continued

Promoter and Enhancer Elements

| Promoter/Enhancer | References |
|---|---|
| HLA DQ and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene et al., 1990 |
| MHC Class II5 | koch et al., 1989 |
| MHC Class II HLD-Dra | Sherman et al., 1989 |
| β-Actin | Kawamoto et al., 1988; Ng et al., 1989 |
| Muscle Creatine Kinase | Jaynes et al., 1988; Horlikc and Benfield, 1989; Johnson |
| Prealbumin (Transthyretin) | Costa et al., 1988 |
| Elastase II | Omitz et al., 1987 |
| Metallothiionein | Karin et al., 1987; Culotta and Hamer, 1989 |
| SV 40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |
| Polyoma | Swartzendruber and Lehman, 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal., 1988 |
| Retroviruses | Kriegler and Botchan, 1982, 1983; Levinson et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 4

Inducible Elements

| Promoter/Enhancer | Inducer | References |
|---|---|---|
| MT II | Phorbol Ester (TFA) Heavy metals | Palmiter et al., 1982; Halinger and Karin, 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee 1981; Majors and Varmus, 1983; Chandler et al., 1983; Lee et al., 1984; Ponta et al., 1985; Sakai et al., 1988 |

TABLE 4-continued

Inducible Elements

| Promoter/Enhancer | Inducer | References |
|---|---|---|
| β-Interferon | poly(rl)x poly (rc) | Tavernier et al., 1983 |
| Advenovius 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV 40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone A Gene | Thyroid Hormone | Chatterjee et al., 1989 |

It may also be desirable to modify the identified regulatory unit by adding additional sequences to the unit. The added sequences may include additional enhancers, promoters or even other genes. Thus one may, for example prepare a DNA fragment that contains the native regulatory elements positioned to regulate one or more copies of the native gene and/or another gene or prepare a DNA fragment which contains not one but multiple copies of the promoter region such that transcription levels of the desired gene are relatively increased.

Turning to the expression of a transgene to produce a protein, once a suitable clone or clones have been obtained, whether they be cDNA based or genomic, one may proceed to prepare an expression system. Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of cDNA version will provide advantages in that the size of the gene will generally be much smaller and more readily employed to transfect the targeted cell than will be a genomic gene, which will typically be up to an order of magnitude larger than the cDNA gene. However, the inventors do not exclude the possibility of employing a genomic version of a particular gene where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

It is proposed that a wild-type, polymorphic or mutant hKIS gene may be co-expressed with wild-type or mutant p27, wherein the proteins may be co-expressed in the same cell or wherein wild-type, polymorphic or mutant hKIS genes may be provided to a cell that already has wild-type or mutant p27. Co-expression may be achieved by co-transfecting the cell with two distinct recombinant vectors, each bearing a copy of either the respective DNA. Alternatively, a single recombinant vector may be constructed to include the coding regions for both of the proteins, which could then be expressed in cells transfected with the single vector. In either event, the term "co-expression" herein refers to the expression of both the wild-type, polymorphic or mutant hKIS and wild-type or mutant p27 proteins in the same recombinant cell.

In addition to co-expression with p27, it is proposed that the wild-type, polymorphic or mutant hKIS gene may be co-expressed with genes encoding other CKI or tumor suppressor proteins or polypeptides. Tumor suppressor proteins contemplated for use include, but are not limited to, the retinoblastoma, p53, Wilms tumor (WT-1), DCC, neurofibromatosis type 1 (NF-1), von Hippel-Lindau (VHL) disease tumor suppressor, Maspin, Brush-1, BRCA-2, and the multiple tumor suppressor (MTS). Further particularly, contemplated is co-expression with a selected wild-type version of a selected oncogene. Wild-type oncogenes contemplated for use include, but are not limited to, tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bcl-2 and family members.

As used herein, the terms "engineered" and "recombinant" cells are intended to refer to a cell into which an exogenous DNA segment or gene, such as a cDNA or gene encoding a hKIS has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

Expression vectors for use in mammalian cells may include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include exogenous origin, such as may be derived from SV40 or other viral (e.g., polyoma, adenovirus, VSV, or BPV) source, or may be provided by the host cell chromosomal replication mechanism. If the vector is integrated into the host cell chromosome, the later is often is sufficient.

The promoters may be from the genome of mammalian cells (e.g., metallothionein promoter) or from mammalian viruses (e.g., CMV immediate early, the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 origin of replication. Smaller or larger SV40 fragments may also be used, providing there is included the approximately 250 bp sequence extending from the HindIII site toward the BglI site located in the viral origin of replication.

In cases where an adenovirus is used as an expression vector, the coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the transgene in infected hosts.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Also, a number of selection systems may be used, including, but not limited to, the herpes simplex virus thymidine kinase, hypoxanthine-guanine phosphoribosyltransferase and adenine phosphoribosyltransferase genes. Also, antimetabolite resistance can be used as the basis of selection for dhfr, that confers resistance to methotrexate; gpt, that confers resistance to mycophenolic acid; neo, that confers resistance to the amonoglycoside G-418; and hygro, that confers resistance to hygromycin.

It is contemplated that a gene of the present invention may be "overexpressed", i.e., expressed in increasing levels of relative to its natural expression in cells. Such overexpression may be assessed by a variety of methods, including semi-quanitative PCR, Northern blotting, RNase protection assays, radio- and Immuno-assays. However, simple and direct methods are preferred, for example, those involving SDS/PAGE and protein staining or western blotting, followed by quantitative analyses, such as densitometric scanning of the resultant gel or blot. A specific increase in the level of the mRNA, recombinant protein or peptide in comparison to the level in natural cells is indicative of overexpression.

Mutagenesis

Certain embodiments of the present invention may require the introduction of mutations into hKIS or a CKI gene. Site-specific mutagenesis provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art and commercial kits are available (AL-TERED SITES® ii in vitro Mutagenesis Systems; Promega Corp., Madison, Wis.). In some cases, the technique employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such s hydroxylamine, to obtain sequence variants.

Proteins and Peptides

The present invention provides purified, and in preferred embodiments, substantially purified proteins and peptides. The term "purified protein or peptide" as used herein, is intended to refer to an aqueous composition, isolatable from mammalian cells or recombinant host cells, wherein the protein or peptide is purified to any degree relative to its naturally-obtainable state, i.e., relative to its purity within a cellular extract. A purified protein or peptide therefore also refers to a protein or peptide free from the environment in which it naturally occurs.

The proteins or polypeptides may be full length proteins or may also be less then full length proteins, such as individual domains, regions or even epitopic peptides. Where less than full length proteins are concerned the most preferred will be those containing the functional domains.

Generally, "purified" will refer to protein or peptide composition that has been subjected to fractionation to remove various other protein or peptide components, and which composition substantially retains the biological activity of the desired protein. For example, a purified wild-type hKIS protein would still maintain biological activity, as may be assessed by binding to p27, forming complexes with p27, or phosphorylating p27.

Where the term "substantially purified" is used, this will refer to a composition in which the protein or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A polypeptide or protein that is "purified to homogeneity," as applied to the present invention, means that he polypeptide or protein has a level or purity where the polypeptide or protein is substantially free from other proteins and biological components. For example, a purified polypeptide or protein will often be sufficiently free of other protein components so that degradative sequencing may be performed successfully.

Various methods for quantifying the degree of purification of proteins or peptides will be known to those of skill in the art in light of the present disclosure. These include, for example, determining the specific biological activity of a faction, or assessing the number of polypeptides within a fraction by gel electrophoresis. Assessing the number of polypeptides within a fraction by SDS/PAGE analysis will often be preferred in the context of the present invention as this is straightforward.

To purify a protein or peptide of interest, a natural or recombinant composition comprising at least some proteins or peptides of interest will be subjected to fractionation to remove various other polypeptide or protein components from the composition. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Although preferred for use in certain embodiments, there is no general requirement that the protein or peptide always be provided in their most purified state. Indeed, it is contemplated that less substantially purified proteins or peptides, which are nonetheless enriched the protein of interest, relative to the natural state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in antibody generation.

Gene Therapy

The general approach to the cell proliferation suppression aspect of the present invention is to provide a cell with a transdominant hKIS protein, a CKI mutated such that it is no longer inhibited by a serine/threonine kinase, or both. By "transdominant hKIS", it is meant that the mutated hKIS or hKIS polypeptide fragment interferes the ability of endogenous hKIS protein to inhibit p27 mediated G1 arrest. While it is conceivable that a protein may be delivered directly to a cell, a preferred embodiment involves providing a nucleic acid encoding a protein to the cell. Following this provision, the polypeptide is synthesized by the transcriptional and translational machinery of the cell, as well as any that may be provided by the expression construct. In providing antisense, ribozymes and other inhibitors, the preferred mode is also to provide a nucleic acid encoding the construct to the cell. All such approaches are herein encompassed within the term "gene therapy".

Viral Vectors

The delivery and entry of recombinant material into target cells is facilitated by use of vectors. DNA can be directly transferred to somatic target cells by viral vectors, such as retroviruses and adenoviruses, and non-viral methods, such as cationic liposomes, liposome viral conjugates, and polymers.

Viruses naturally infect mammalian cells and introduce their viral DNA to convert the host biosynthetic pathway to produce viral DNA, RNA, and protein. Molecular biologists have been able to modify these viruses so that they deliver foreign DNA to the target cell but cannot replicate in the host cell nor express viral proteins necessary for encapsulation. In general, early response viral sequences, involved in viral transcription, translocation or capsid synthesis, have been removed from the viral genome and are replaced by the foreign gene of interest.

Therefore, these recombinant viruses can only propagate in specific packaging cell lines which express the deleted viral proteins. Replication-deficient retroviruses, adenoviruses, adeno-associated viruses and adenoviral conjugates are now used in gene transfer techniques.

Retroviruses are RNA viruses that require vector integration into the host genome for expression of the transgene thus limiting their use to dividing cells. As most of the vascular and myocardial cellular components are non-replicating cells, retroviruses are of limited use in cardiovascular gene transfer. In addition, integration at random locations may lead to insertional mutagenesis and transformation. However, there have been no reported short- or long-term toxicity associated with their use in human gene therapy trials. Retrovirus-mediated gene transfer has been used for cell-mediated gene transfer using endothelial cells and for direct gene transfer into porcine arteries. The long-term, high-level expression renders retroviral vectors in particular ideal for ex vivo, cell-mediated gene transfer.

In cell-mediated gene transfer, endothelial cells or vascular smooth muscle cells may be isolated, expanded and transduced in the laboratory and reseeded on to an artery in vivo. The technique of ex vivo gene transfer is however fairly cumbersome since it requires cell expansion. However, ex vivo gene transfer of endothelial cells and smooth muscle cells may be useful in seeding stents, grafts or injured arteries during vascular procedures to treat thrombotic disorders or graft hyperplasia.

Recombinant gutted lentiviruses may represent an attractive alternative to retroviruses. Lentiviruses have not been directly implicated in any malignancies and, in contrast to retroviral based vector systems, human, simian and bovine immunodeficiency viral (HIV, BIV, SIV) vector systems have been shown to mediate stable gene transfer in terminally differentiated neurons and macrophages in culture. In vivo, transgene expression is detected for up to 6 months in liver, muscle, retinal tissue, and brain of immune-competent rats in vivo and does not appear to evoke an immune response or local inflammation, permitting repeated viral challenge.

Recombinant adenoviruses efficiently transfect proliferating and non-proliferating cells, but lack mutagenicity since the transgenic genome is not integrated into the host chromosome but remains episomal. Deletions of EI A, EI B, E2 and E3 regions of the viral genome prevent viral replication in transfected cells, reduce expression of early response viral proteins, and hence, limit cellular inflammation. Recombinant adenoviruses have been successfully used for in vivo gene transfer in carotid and jugular veins rat and rabbit myocardium and rabbit peripheral arteries. In vivo adenovirus-mediated gene transfer using biological active gene products have also been shown to exert effects in vascular diseases. Since immunogenicity remains limiting in adenoviral vectors, adenoviral vectors gutted of almost the entire adenoviral genome may prove to be beneficial in circumventing the deleterious immune response.

Recombinant adeno-associated viruses (rAAV) are promising vectors given the ability to integrate into the host genome, resulting in stable transgenic expression, and lack of immunogenicity due to a lack of viral genes in the vector that express surface proteins. rAAV vectors are described in U.S. Pat. No. 5,139,941. rAAV has not been associated with disease in any host and has not been associated with malignancies despite integration of the transgene into the host genome. rAAV integrates viral and transgenic DNA preferentially but not exclusively at chromosome 19q locus. Adeno-associated viruses are incapable of replication and depend on co-infection with adenovirus or a herpes virus for replication. In vivo, long-term expression of β-galactosidase and tyrosine hydroxylase have been achieved in non-dividing neurons in the rat CNS by rAAV, and intravenous delivery of rAAV encoding human clotting factor IX resulted intransduction of 3% of all hepatocytes over a 5 month observation period. Also, intraluminal and periadventitial vascular delivery of rAAV in atherosclerotic carotid arteries of cynomolgus monkeys results in efficient transgenic expression. However, in contrast to retroviruses and adenoviruses, transgenic expression is predominantly found in adventitial endothelial cells of microvessels.

Other viral vectors that may be used for gene therapy include herpes simplex virus (U.S. Pat. No. 5,288,641) and cytomegalovirus (Miller, 1992).

Non-Viral Vectors

Because of safety concerns regarding viral vectors, an interest arose in developing synthetic delivery system avoiding the infectious complications presented by the first generation viral vectors. Non-viral gene transfer can be performed by microinjection, DEAE-dextran transfection, calcium phosphate precipitation, electroporation, liposomes, and particle-mediated gene transfer (i.e. introducing DNA-coated particles).

The most common non-viral gene transfer vectors are DNA-liposomes. Cationic liposomes condense and entrap the DNA through electrostatic interaction. They are prepared by sonification and remain stable in aqueous solution for months. The positively charged liposome complex fuses with the negatively charged cell surface to release the DNA into the cytoplasm of target cells, bypassing the lysosomal compartment and degradation by serum. It is postulated that plasmid DNA is subsequently incorporated in the nucleus as an episome. The relatively safe profile of liposomes, the lack of vector size or target cell constraints, as well as the relative ease of liposome-DNA complex preparation favors this gene transfer technique.

Preclinical studies using different forms of these lipids (DOTMA, DC-Chol, DMRIE, and DLRIE) have shown promise for efficient in vivo transfection. Lipofection-mediated gene transfer, using either catheter-based delivery or direct injection, results in site-specific expression of foreign recombinant genes in vascular endothelial and smooth muscle cells and alters the biology of the vessel wall. Cationic liposomes are well tolerated in vivo and do not induce any biochemical, hemodynamic or cardiac intoxications.

Additional advances in lipid chemistry are developing newer generations of cationic liposomes, which permit higher transfection with minimal toxicity. The transfection efficacy and specificity of lipofection may be further augmented by coupling of ligands or viral particles (Ad, HVJ, VSVG) to the liposomes. In particular, HVJ-coated liposomes have been successfully utilized to transduce venous bypass grafts ex vivo and in vivo.

In certain embodiments, plasmid DNA or RNA may be injected directly into tissue such as skeletal muscle or myocardium. In other embodiments, anti-sense oligonucleotides are used for gene therapy (Morishita et al., 1993). Anti-sense oligonucleotides do not require a vector for cell transduction and can be directly injected in the target tissue. Anti-sense oligonucleotides are short DNA sequences complementary to the RNA message of interest, which are chemically modified to resist nuclease degradation. The oligonucleotide may be modified at the 5; end to prevent nuclease degradation or may made up of ribonucleotide bases attached to a peptide backbone (protein nucleic acid).

Various animal and cell culture studies have shown that anti-sense oligonucleotides are able to efficiently modify intracellular expression of factors involved in smooth muscle cell and endothelial cell migration and proliferation, including by use of anti-sense oligonucleotides against c-myc, c-myb, cdc2, and PCNA. The nucleotide sequence hybridizes to target RNA, which prevents translation of RNA, targets the message for degradation by ribonuclease H, and interferes with cytosolic translocation.

Gene Transfer in the Cardiovascular System

In certain embodiments of the present invention, gene therapy is used to treat or prevent cell proliferation. In preferred embodiments, vascular cell proliferation such as that associated with restenosis or atherosclerosis is prevented using gene therapy. It is contemplated that a gene therapy vector or composition of the present invention may be tested in an animal model. Studies in animal models of cardiovascular disease have demonstrated that transgenes can be expressed at high levels at local sites in the vasculature.

Local Delivery to the Vasculature

An attractive feature of cardiovascular gene transfer is that recombinant genes may be delivered to local sites in the vasculature by a medical device. Medical devices that are suitable for use in the present invention include known devices for the localized delivery of therapeutic agents. Such devices include, for example, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935,114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS™ (Scimed Life Systems, Inc.), the SYMPHONY® (Boston Scientific Corporation), the Wallstent (Schneider Inc.), the Precedent II™ (Boston Scientific Corporation) and the NIR™ (Medinol Inc.). Such devices are delivered to and/or implanted at target locations within the body by known techniques.

The double balloon catheter was an initial catheter employed in animal model studies and was useful to demonstrate the basic principles of gene transfer. The catheter consists of two balloons placed about 1.5 cm apart with an inner protected space. The genetic vector is instilled into the isolated arterial segment between the balloons. Adenoviral-mediated recombinant gene expression is detected in endothelial cells, vascular smooth muscle cells and adventitial cells for several weeks following infection and is not found downstream to the arterial segment or in other tissues by PCR. Retroviral-mediated gene expression can be detected for up to 6 months. A disadvantage to this catheter is the possibility of distal ischemia due to occlusion of blood flow. Alternate delivery devices permit flow distal to the isolated segment allowing a prolonged instillation time period without compromising distal perfusion.

Porous and microporous balloons infuse the vector directly into the juxtapositioned arterial wall through small pores in the catheter. The depth of delivery is directly related to the perfusion pressure. Channel balloon catheters combine two separate inflatable compartments for balloon angioplasty and drug infusion, allowing separate control of balloon inflation pressure for positioning and drug infusion pressure. A hydrogel coated balloon catheter has a hydrophilic polyacrylic acid polymer coating of the balloon. This polymer absorbs the DNA suspension and when the balloon is inflated, the DNA coating is pressed against the vessel wall. The iontophoretic balloon uses a local current between the balloon and the skin of the subject to drive the negatively charged DNA into the arterial wall.

Other delivery devices include stents coated with a DNA-impregnated polymer or cells comprising a nucleic acid of the present invention (ex vivo gene transfer) into arterial and venous grafts. Furthermore, tissue may be selectively targeted for gene therapy by use of tissue specific promoters and enhancers.

Expression Constructs in Combination with Other Therapies

The method of the present invention can be combined with other methods for treating cell proliferation. For example, other genes such as thymidine kinase, cytosine deaminase, wild-type or mutated p21, p27, and p53 and combinations thereof can be concomitantly transformed into cells and expressed. For example, the herpes simplex-thymidine kinase (HS-tK) gene, when delivered to blood vessel walls by a adenoviral vector system, successfully resulted in the decrease in neointimal proliferation associated with restenosis (Chang et al., Mol. Med., 1995, 172-181). In the context of the present invention, it is contemplated that mutant hKIS or CKI gene expression could be used similarly in conjunction with other gene therapy approaches. The genes may be encoded on a single nucleic acid but separately transcribed. Alternatively, the genes may be operably linked such that they are contranscribed. In preferred embodiments, the genes are operably linked to encode a fusion protein. In other embodiments the co-transcribed genes are separated by an internal ribosome binding site allowing the proteins to be translated separately. Such combination therapies are described in WO 99/03508 (incorporated herein by reference in its entirety).

Myocardial Delivery

In certain embodiments of the present invention, nucleic acid or protein compositions of the present invention may be introduced into the myocardium. Myocardial gene transfer requires tranfection of terminally differentiated myocytes. Adenoviral gene transfer by intracoronary or intramyocardial delivery results in transient gene expression for several weeks in a limited number of cells. Adeno-associated viral vectors have been shown to induce stable transgene expression in up to 50% of murine, rat and porcine cardiomyocytes after ex vivo intracoronary infusion and myocardial injections for at least 6 months. These vectors may be useful for gene delivery to treat human myocardial diseases.

Vascular Diseases

Many vascular diseases are characterized by abnormalities of cell proliferation. One approach to therapies is to express genes that inhibit cell proliferation within vascular lesions, for example, after angioplasty or in a by-pass graft. Most approaches regulate the cell cycle in vascular smooth muscle, endothelial or macrophage cells.

Progression through the cell cycle is regulated by the assembly and phosphorylation of cyclin/cyclin-dependent kinase complexes (CDKs). Endogenous inhibitors of the cyclin-CDKs, termed the cyclin-dependent kinase inhibitors (CKIs) result in cell cycle arrest and cessation of cell proliferation.

Genetic strategies to abrogate vascular lesion formation have focused on regulatory gene products that interfere with DNA synthesis, cell cycle progression, and cell viability. Gene products interfering with DNA and RNA replication have been evaluated for their capacity to block smooth muscle cell proliferation and reduce vascular lesion formation. Pro-drug-enzyme therapies, using thymidine kinase or cytosine deaminase, constitute a form of local therapy in which an enzyme is expressed locally that converts a prodrug into an active form. Gene transfer of DNA encoding these converting enzymes to the injured arterial wall combined with systemic prodrugs administration produces high levels of growth inhibitory drugs in the target tissue. The therapeutic effect of transgene expression can be regulated by administration of the prodrug and can be initiated independently of the gene transfer.

Herpes simplex virus thymidine kinase (HSV-tk) converts an inert nucleoside analog, ganciclovir into a phosphorylated, toxic form in transduced cells. Its subsequent incorporation into the host DNA induces chain termination and cell death in dividing cells, while non-dividing cells remain unaffected. Local delivery of recombinant adenovirus encoding for HSV-tk at the time of the balloon injury and systemic administration to ganciclovir inhibited smooth muscle cell proliferation in vivo, and decreased intimal formation in balloon-injured porcine and rat arteries and atherosclerotic rabbit arteries. A similar reduction of neointimal hyperplasia was observed in arterial interposition grafts which overexpress HSV-tk in the rabbit. Cytosine deaminase (CD) catalyzes the hydrolytic deamination of non-toxic cytosine and 5-fluorocytosine (5-FC) into uracil and 5-fluorouracil, which inhibits thymidilate synthase and hence DNA and RNA synthesis. In human and rabbit primary smooth muscle cells, CD/5-FC does not induce significant necrosis or apoptosis but results in cytostatic effects on vascular smooth muscle cells. CD gene transfer in the rabbit femoral injury model followed by systemic 5-FC treatment resulted in a decrease of the intima to media area ratio, comparable to the efficacy of HSV-tk/ganciclovir in a rat and pig model of vascular injury.

The Fas/FasL death-signaling pathway mediates cellular immunocytotoxicity in activated lymphocytes. Binding of the Fas receptor to FasL activates the caspase pathway leading to apoptosis. FasL is expressed in intimal smooth muscle cells and immune competent cells in atherosclerotic plaques. Studies using adenoviral-mediated gene transfer of FasL to balloon-injured rat carotid arteries demonstrated an attenuation of T cell extravasation in FasL expressing arteries as opposed to sham virus treated arteries, accompanied with a 60% reduction of neointima formation (intima/media area ratio). FasL may function to protect the vessel from leukocyte extravasation to the subendothelial space during arterial repair by inducing T lymphocyte apoptosis.

Targeting of cell cycle regulatory proteins promotes inhibition of cell proliferation, and cell differentiation. Cell cycle arrest prevents vsmc proliferation and migration and endothelial dysfunction, shown by improved vasoreactivity and NO production, rendering the vessel less susceptible to inflammatory infiltration and free radical formation.

Progression through the cell cycle is controlled by the assembly and disassembly of the different cyclin-cyclin dependent kinase complexes. These complexes phosphorylate retinoblastoma protein leading to the release of the sequestered transcription factors, E2F and Elf 1. The cyclin dependent kinase inhibitors (CKIs) modulate the enzymatic activity of cyclin/CDK complexes necessary for $G_1$ progression. In vivo, Ad-p21 infection of porcine iliofemoral and rat carotid arteries following balloon injury reduces BrdU incorporation by 35% and I/M area ratio by 37%. Likewise, Gax homeobox gene overexpression, as an upstream regulator of p21, in the rat carotid artery injury model inhibited neointimal formation and luminal narrowing by 59 and 56 percent, respectively. Adenovirus-mediated overexpression of p27 in balloon-injured rat and porcine arteries significantly attenuated intimal lesion formation.

The effects of many cyclin-CDK and CKI interactions are mediated through their effect on the phosphorylation status and therefore activity of retinoblastoma gene product (Rb). Rb inhibits cell cycle progression from $G_1$ into S phase by sequestering and inactivating a set of cellular transcription factors. Localized infection of porcine endothelial cells and vsmc with Ad-ΔRb, an unphosphorylatable, constitutively active Rb, results in a significant reduction in cell proliferation and [$^3$H]thymidine incorporation, yet the cells remain viable. In the rat carotid artery injury as well as in the pig balloon injury model, ΔRb expression results in a 42-47% decrease in the neointima/media area ratio relative to control arteries.

Alternatively, inhibition of the cell cycle in human vein grafts with ex vivo treatment of E2F decoy oligodeoxynucleotide reduces not only graft susceptibility to atherosclerosis, and enhances medial hypertrophy, which renders the graft more resistant to increased hemodynamic stress and improves vein graft patency.

Metalloproteinases degrade the extracellular matrix, promote growth factor release and cell activation and are therefor essential for cell migration. Overexpression of tissue inhibitor of metalloproteinases (TIMP) was shown to inhibit invasive and metastatic behavior of tumor cells. The effects of TIMP protein expression has been evaluated in an organ culture model of neointimal formation, which lends itself for the study of smc migration rather than proliferation. Overexpression of TIMPi and 2 reduced neointima formation and neointimal cell numbers by 54-79% and 71% respectively, but did not alter smc proliferation and viability. These data confirm the importance of metalloproteinases and smc migration to the development of neointimal hyperplasia and suggest that a combined anti-proliferative and anti-migratory gene therapy approach may optimize lesion reduction.

Other methods aim to reconstitute endothelial derived inhibitory signals, which prevent leukocyte adhesion and platelet aggregation, relax local muscle tone and inhibit vsmc proliferation by gene transfer of iNOS or eNOS. The NOS pathway has been shown to play a significant role in a number of cardiovascular disorders including atherosclerosis, systemic and pulmonary hypertension, ischemia-reperfusion, hypercholesterolemia, and vasospasm. L-arginine feeding, iNOS and eNOS gene transfer and various NO donors have shown to successfully reduce lesion formation in hypercholesterolemic rabbits and neointimal hyperplasia following arterial balloon injury model in pigs and rats.

Thus, studies in various animal models demonstrate that genetic approaches are feasible and effective in limiting cell proliferation, migration and extracellular matrix deposition. The nucleic acids and proteins or polypeptides of the present invention may be particularly useful in methods of treating cardiovascular disease. For example, a nucleic acid encoding a transdominant hKIS or mutated CKI may be introduced locally into an injured artery to prevent restenosis. In a preferred embodiment, a vector comprising both a trandominant hKIS and a mutated p27 is used to treat restenosis. Of course, both genes may be introduced together but in separate vectors.

In other embodiments, gene therapy using a nucleic acid of the present invention may be combined with other gene and non-gene therapies to treat a cardiovascular disease. Potential molecular targets for cardiovascular disease are shown in Table 5.

TABLE 5

Potential molecular targets for cardiovascular disease

| Pathophysiology | Molecular Target |
| --- | --- |
| Endothelial dysfunction & endothelial injury | NOS-NO donors VEGE; FGF, Fas-L |
| Abnormal smc proliferation | CKIs, E2F decoy, Rb mutants, TK/ganciclovir; cd/5-fluorocytosine; FasL |
| Thrombosis | Tissue factor inhibitors; antithrombin agents |
| Abnormal smc migration | Metalloproteinase inhibitors (TIMP); plasminogen activator inhibitors |
| Abnormal apoptosis | Bcl-2 inhibitors, Bax or CPP32 inducers |
| Plaque rupture | Metalloproteinase inhibitors; leukocyte adhesion blockers |
| Neoangiogenesis | a/bFGF; VEGF; Angiopoietin |
| Dyslipidemia | LDL-R, ApoE, ApoA, LPL |
| Systemic/Pulmonary Hypertension | NOS-NO donors |

TABLE 5-continued

Potential molecular targets for cardiovascular disease

| Pathophysiology | Molecular Target |
| --- | --- |
| Graft failure | NOS - NO donors; TPA; FasL; E2F decoy; TGFβ |
| Heart failure | Bcl-2 inhibitors, Bax or CPP32 inducers MyoD; fetal myocyte transplant; $β_2$ adrenergic receptor/ $β_2$ adrenergic receptor kinase SR Ca(2+) pumps |

Pharmaceutical Compositions

Pharmaceutically Acceptable Carriers

Aqueous compositions of the present invention comprise an effective amount of a compound dissolved or dispersed in a pharmaceutically acceptable carrier or aqueous medium. Aqueous compositions of gene therapy vectors are also contemplated. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, subcutaneous, intralesional, or even intraperitoneal routes.

The pharmaceutical forms suitable for local administration of a composition of the present invention include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A composition of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, an liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In terms of using peptide therapeutics as active ingredients, the technology of U.S. Pat. Nos. 4,601,903; 4,559,231; 4,559,230; 4,596,792; and 4,578,770, each incorporated herein by reference, may be used.

The preparation of more, or highly, concentrated solutions for direct administration is also contemplated, where the use of DMSO as solvent is envisioned to result in extremely rapid penetration, delivering high concentrations of the active agents to a small tumor area.

Kits

The composition of the present invention may be included in kits. Kits may comprise compositions comprising various components made using the present invention such as for example, cells, expression vectors, virus stocks, proteins, antibodies, catheters, coated stents, and drugs. These components may be in a form appropriate for the intended application. Generally, this will entail preparing compositions that are essentially free of pyrogens, as well as other impurities that could be harmful to humans or animals. Such kits may include a nucleic acid encoding a CKI serine/threonine mutant and/or a trandominant hKIS mutant.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes of practice. However, those of skill in the art should, in light of the present disclosure, appreciate that many changes can be made in the specific embodiments which are disclosed and still obtain a like or similar result without departing from the spirit and scope of the invention.

Example 1

Identification of hKIS a Serine/Threonine Kinase that Interacts with p27 Cyclin-Dependent Kinase Inhibitor Using a yeast two-hybrid screen, cDNAs from a human B-cell library (Elledge, 1993), encoding proteins that interact with p27$^{Kip1}$. To obtain genes other than cyclins and cyclin-dependent kinases that are abundant in the library, the COOH-terminal domain of p27$^{Kip1}$ fused to the DNA-binding domain of the GAL4 transcription activator was used as bait (Sherr, 1994). This COOH-terminal domain is conserved between p27$^{Kip1}$ and p57$^{Kip2}$ and contains a nuclear translocation signal and phosphorylation site for cyclin E/Cdk2 (Polyak et al., 1994; Sheaff et al., 1997; Matsuoka, 1995). In contrast to the NH$_2$-terminal domain, the COOH-terminal domain is inactive as a CDK inhibitor (CKI), but it has been assumed to play a role in protein-protein interactions (Maucuer, 1997).

The yeast-two hybrid screen was performed according to the Matchmaker Two-Hybrid system protocol (Clontech, Palo Alto, Calif.) using pGBT9 p27$^{Kip1}$COOH as bait. As prey, a human B-cell library (Elledge, 1993) fused to the GAL4 activating domain was used. Positive yeast clones were identified by prototrophy for histidine and expression of β'-galactosidase gene. The yeast plasmid DNA from the positive clones was isolated and transformed into *Escherichia coli*. Subsequently, interactions were tested by direct cotransfection of GAL4 DNA-binding-domain-fused genes and the positive clones (fused to the GAL4 activating domain) into *Saccharomyces cerevisiae*. Both strands of the cDNAs were sequenced. Identification of the sequence and sequence comparisons were performed using the National Center for Biotechnology Information (NCBI) on-line service.

The yeast two-hybrid screen yielded several cDNAs that interacted with the p27$^{Kip1}$ COOH-terminal domain, but not the NH$_2$-terminal region of p27$^{Kip1}$, p57$^{Kip2}$, or p21$^{Cip1}$ (FIG. 1). The clones interacted with full-length p27$^{Kip1}$ as well as the COOH-terminal domain of p27$^{Kip1}$ in yeast. The entire coding sequence of one clone (SEQ ID NO:1), C21, encodes a polypeptide that was 99% similar to the rat serine/threonine protein kinase KIS (Maucuer et al., 1997; Genbank Acc. No. X98374). Based on this identity, it was concluded that this clone was the human homologue of rat KIS (hKIS). The 46.5 kDa hKIS (SEQ ID NO:2) protein consists of an NH$_2$-terminal serine/threonine kinase consensus region and a COOH terminal region with 42% sequence similarity to hU2AF65, a 65 kDa subunit of the splicing factor U2AF (Zamore, 1992). hKIS binding was specific for COOH-terminal p27$^{Kip1}$, because it failed to interact in the two hybrid assay with NH$_2$-terminal p27$^{Kip1}$, p57$^{Kip2}$, p21$^{Cip1}$ and several negative controls.

The specificity of the interaction between hKIS and p27$^{Kip1}$ was analyzed further biochemically. In vitro translated $^{35}$S-methionine-labeled hKIS was incubated with glutathione S-transferase (GST), GST-p16$^{Ink4}$, GST-p27$^{Kip1}$, GST-p21$^{Cip1}$, or GST-p57$^{Kip2}$ (Morgan, 1995). hKIS directly bound GST-p27$^{Kip1}$, but not the other cyclin-dependent kinase inhibitor fusion proteins.

To determine the function of hKIS, epitope-tagged in vitro translated hKIS was immunoprecipitated and incubated with purified recombinant p27$^{Kip1}$ in the presence of $^{32}$P-ATP (Zamore, 1992). In contrast to a negative control extract, hKIS readily phosphorylated bacterial-produced p27$^{Kip1}$. Under the same conditions, hKIS did not phosphorylate p57$^{Kip2}$, p21$^{Cip1}$ or p16$^{Ink4}$, documenting the specificity of p27$^{Kip1}$ phosphorylation by hKIS. In addition, hKIS was also observed to undergo autophosphorylation.

To localize the hKIS phosphorylation site on p27$^{Kip1}$, hKIS was incubated in an in vitro phosphorylation assay with NH$_2$-terminal or COOH-terminal GST-p27$^{Kip1}$. Though hKIS was found to bind the COOH-terminal domain of p27$^{Kip1}$, phosphorylation of GST-p27$^{Kip1}$ was detected in the NH$_2$.terminal region of the protein. To localize the phosphorylation site further, mutational analyses were performed in this region. Specifically, mutation of serine 10 to alanine (S10A) abolished phosphorylation of GST-p27$^{Kip1}$, indicating that this amino acid is required for hKIS kinase activity on p27$^{Kip1}$. Serine 10 to alanine mutation does not affect in vitro binding of p27$^{Kip1}$ (S10A) with hKIS.

To determine the subcellular localization of hKIS, immunofluorescence and subcellular fractionization studies were performed. An hKIS-green fluorescent protein (GFP) fusion protein was prepared and transfected into 293 cells. In contrast to GFP alone, which showed characteristic cytoplasmic staining, hKIS-GFP localized predominantly in the nucleus. This localization was confirmed by biochemical analysis of epitope-tagged hKIS in nuclear and cytoplasmic extracts. Endogenous p27$^{Kip1}$ was detected in both compartments, though at higher levels in the nucleus. In contrast, hKIS localized primarily to the nucleus. In addition, endogenous p27$^{Kip1}$ and hKIS were found to associate biochemically in vivo in nuclear extracts, as determined by immunoprecipitation with anti-p27$^{Kip1}$ antibody, followed by detection of hKIS by Western blot analysis.

To determine whether hKIS alters cell cycle progression regulated by p27$^{Kip1}$ in vivo, cell transfection studies were performed. A human melanoma line, UM316, was transfected with hKIS, p27$^{Kip1}$ or p21$^{Cip1}$, alone or in various combinations. Human CD2 was included as a marker for cell transfection to facilitate cell cycle analysis (Hannon and Beach, 1999; Danthinne et al., 1999). Transfection of hKIS alone did not alter cell cycle distribution, but p27$^{Kip1}$ arrested cells at the G1/S checkpoint as expected. Importantly, cotransfection of hKIS and p27$^{Kip1}$ reversed the growth arrest by p27$^{Kip1}$, indicating that hKIS is a negative regulator of p27$^{Kip1}$. In contrast, cotransfection of hKIS with a p21$^{Cip1}$ vector had no effect on cell cycle progression, documenting the specificity of the interaction between hKIS and p27$^{Kip1}$ in vivo.

In order to demonstrate that hKIS regulates p27$^{Kip1}$ by phosphorylation of serine 10 of the p27 amino acid sequence, we performed similar cell cycle studies by adding the kinase inactive hKIS (K54R; SEQ ID NO:4) and p27$^{Kip1}$ (S10A; SEQ ID NO:6) which is not phosphorylated by hKIS in vitro.

To confirm the results in UM316 cells in another cell line, NHI 293 cells were transfected with hKIS (K54R), p27$^{Kip1}$, p27$^{Kip1}$ (S10A) mutant, alone or in various combinations. Human CD2 was included as a mark for cell transfection to facilitate cell cycle analysis. Transfection of hKIS and hKIS (K54R) alone did not alter cell cycle distribution, but p27$^{Kip1}$ as well as p27$^{Kip1}$ S10A arrested cells at the G1/S checkpoint as expected. In this different cell line, it was confirmed that cotransfection of hKIS and p27$^{Kip1}$ reversed the growth arrest by p27$^{Kip1}$. In contrast, cotransfection of hKIS with p27$^{Kip1}$ (S10A) as well as hKIS (K54R) with p27$^{Kip1}$ had no effect on the ability of hKIS to arrest cells at the G1/S checkpoint, suggesting that phosphorylation of serine 10 by hKIS is important in regulating p27$^{Kip1}$ functions.

Example 2

Construction of Expression Vectors

The expression vectors of Example 1 were constructed as follows. pGBT9p27$^{Kip1}$CR, pGBT9p27$^{Kip1}$NH$_2$ and pGBT9p27$^{Kip1}$COOH were obtained by PCR amplification (p27$^{Kip1}$CR: p27$^{Kip1}$CR5'P CGT <u>GAATTC</u> ATG TCA AAC GTG CGA GTG (SEQ ID NO:7) and p27$^{Kip1}$CR3'P CGT <u>GGATCC</u> TTA CGT CTG GCG TCG AAG GCC (SEQ ID NO:8); P27$^{Kip1}$NH$_2$: p27$^{Kip1}$CR5'P and p27$^{Kip1}$NH$_2$3'P CTG <u>GGATCC</u> TGT AGA ACT CGG GCA AGC T (SEQ ID NO: 9); p27$^{Kip1}$COOH: p27$^{Kip1}$COOH5'P CTG <u>GAATTC</u> TTA GCG GAG CAG TGT CCA (SEQ ID NO:10) and p27$^{Kip1}$CR3'P) and subcloned into pGBT9 (Clontech, Palo Alto, Calif.) following digestion with EcoR1 and BamH1.

pGBT9p57 and pGBT9p21 were generated by PCR amplification (pGBT9p57: p57 5'P CGT <u>GAATTC</u> ATG GAA CGC TTG GCC TCC (SEQ ID NO:11) and p57 3'P CGT <u>GGATCC</u> TCA AGA GTC TGC AAA CGC GC (SEQ ID NO:12); pGBT9p21: p21 5'P CGT <u>GAATTC</u> GGC ACC ATG TCC AAT CCT (SEQ ID NO:13) and p21 3'P CTG <u>GTCGAC</u> GTG GGC ACT TCA GGG TTT (SEQ ID NO:14) and subcloned into pGBT9 following digestion with EcoRI/BamH1 for p57 and EcoRi/SalI for p21.

The glutathione S-transferase (GST) fusion-gene plasmids pGSTp27$^{Kip1}$, pGSTp27$^{Kip1}$NH$_3$, pGSTp27$^{Kip1}$COOH, pGSTp2I$^{Cip1}$ and pGSTp57$^{Kip2}$ were constructed by EcoRI/SalI digestion of pGBT9p27$^{Kip1}$CR, pGBT9p27$^{Kip1}$NH$_2$, pGBT9p27$^{Kip1}$COOH, pGBT9p21$^{Cip1}$, pGBT9 p57$^{Kip2}$ and ligated into the EcoRI/SalI site of pGEX-6P (Pharmacia, Piscataway, N.J.). pGSTp27$^{Kip1}$ NH2S10M was cloned by PCR amplification (p27$^{Kip1}$NH$_3$S10M5'P GCT GGA TCC ATG TCA AAC GTG AGA GTG TCC AAC GCT CCG AG (SEQ ID NO:15)(Serine10 AGC→Alanine GCT) and p27$^{Kip1}$NH$_2$3'P) and subcloned into BamHI site of pGEX-6P. pGST p16$^{Ink4}$ was obtained by EcoRI/XhoI digestion of BShp16 and subcloned into EcoRI/XhoI digested pGST-6P. The 3'end of hKIS cDNA was mapped by rapid amplification of cDNA ends (RACE) with internal primers for hKIS and total RNA from JY-cells by using 3'RACE system (GIBCO, Gaithersburg, MID). The hKIS cDNA was cloned into the XhoI site of pcDNA3.1/His (Invitrogen, Carlsbad, Calif.). pVR1012hKIS was obtained by XhoI/Xba digestion of pcDNA3.1hKIS and subcloned into the SalI/Xba site of VCL1012CMV (Vical, San Diego, Calif.). The plasmids pVR1012p2I, pVR1012p27$^{Kip1}$, and pVRCD2 were described elsewhere (Serrano, 1995).

Example 3

In Vitro Translation and Transcription

[$^{35}$S]-methionine-labeled and unlabeled hKIS were produced by in vitro transcription/translation using the TNT T7-coupled reticulocyte lysate system (Promega, Madison, Wis.) with pcDNA3.1KIS as the template. The crude cell lysate of the GST-fused proteins was prepared according to the manufacturer's protocol (Pharmacia, Piscataway, N.J.). The fusion proteins were bound to gluthathione-Sepharose™-4B beads (Pharmacia Biotech, Uppsala Sweden) in IP buffer containing 250 mM KCL, 2.5 mM MgCl$_2$, 20 mM Hepes pH7.9, 0.1% NP4O and IxComplete™ protease inhibitor cocktail (Boehringer, Mannheim, Germany). After 1 hour incubation at 4° C., the beads were washed three times.

Binding assays were performed by incubating GST-fusion protein with 20 μg [$^{35}$S]-methionine-labeled hKIS transcription/translation mixture at 4° C. for 1 hour in IP buffer and washed 3 times. The bound proteins were analyzed by SDS-poly acrylamide gel electrophoresis (SDS-PAGE). To confirm the correct size and amount of GST-fusion proteins, the PAGE was stained with Coomassie Brilliant Blue R250 (GIBCO, Gaithersburg, Md.) prior to visualizing the [$^{35}$S]-methionine labeled hKIS by autoradiography.

The GST-fusion proteins were digested with PreScission™ protease (Pharmacia, Piscataway, N.J.) according to the manufacturer's protocol. The in vitro phosphorylation assay was carried out by incubation of CKIs with immunoprecipitated hKIS at 30° C. for 30 minutes in 20 μl phosphorylation buffer (20 mM Tris/HCl pH7.5, 1 mM EGTA, 10 mm MgCl$_2$, 1 mM dithiothreitol, Ix Complete™ protease inhibitor cocktail and 10 μCiγ$^{32}$P-ATP. The samples were analyzed by SDS-PAGE.

Example 4

Cell Culture and Transfection 293 cells were maintained in Dulbecco's modified Eagle's medium (GIBCO, Gaithersburg, Md.) containing 10% fetal bovine serum (FBS), glutamine (2 mM) plus antibiotics. UM316 cells, JY-cells and a human transformed B cell line were cultured in RPMI 1640 medium (GIBCO, Gaithersburg, Md.) supplemented with 10% FBS, glutamine (2 mM) and antibiotics. Cell transfection was performed at 40% confluency using Lipofectamine (GIBCO, Gaithersburg, Md.) according to the manufacturer's instructions. Four hours after transfection, the cells were split.

REFERENCES

Chien, Bartel, Sternglanz, Fields, "The two-hybrid system: A method to identify and clone genes for proteins that interact with a protein of interest," *Proc. Natl. Acad. Sci. USA*, 88:9578-9582, 1991.

Chou and Fasman, "Conformational Parameters for Amino Acids in Helical, β-Sheet, and Random Coil Regions Calculated from Proteins," *Biochemistry*, 13(2):211-222, 1974b.

Coats et al., *Science*, 272:877, 1996.

Danthinne, K. Aoki, A. Kurachi, G. Nabel, E. Nabel, *J. Virol.* 72, 9201(1999).

Durfee et al., "The retinoblastoma protein associates with the protein phosphatase type 1 catalytic subunit," *Genes Dev.*, 7:555-569, 1993.

Elledge, et al., *Genes & Dev.* 7, 555 (1993).

Fields and Song, "A novel genetic system to detect protein-protein interactions," *Nature*, 340:245-246, 1989.

Hannon, D. Beach, *Nature* 371, 257 (1999).

Harper et al., *Cell*, 75:805, 1993.

Hartwell, *Science*, 183:46-51, 1974.

Hopps, U.S. Pat. No. 4,554,101.

Matsuoka, et al., *Genes Dev.* 9, 650 (1995).

Maucuer et al., *J. Biol. Chem.*, 272(37):23151-23156, 1997.

Miller, *Curr. Top. Microbiol. Immunol.*, 158:1, 1992.

Morgan, *Nature* 374, 131 (1995).

Morgan, *Nature*, 374:171, 1995.

Morishita et el., *Trans. Assoc. Am. Phys.* 106:56-61, 1993.
Nurs, *Nature,* 344:503-508, 1990.
Polyak et al., *Cell,* 78:59, 1994.
Toyoshima and Hunter, *Cell,* 78:67, 1994.
Sambrook, Fritsch, Maniatis, Molecular Cloning: *A Laboratory Manual,* 2$^{nd}$ Ed., Cold Harbor Press, Cold Spring Harbor, N.Y., 1989.
Serrano et al., *Nature,* 366:704, 1993.
Serrano, B. Gómez-Lahoz, R. A. DePinho, D. Beach, D. Bar-Sagi, *Science* 267, 249(1995).
Sheaff, M. Groudine, M. Gordon, J. Roberts, B. E. Clurman, *Genes Dev.* 11, 1464 (1997).
Sherr and Roberts, *Genes. Dev.,* 9:1149, 1995.
Sherr, *Cell,* 79:551, 1994.
Sherr, *Science,* 274:1672, 1996.
Xiong et al., *Nature,* 366:701, 1993.
Zamore, J. G. Patton, M. R. Green, *Nature* 355, 609 (1992).

The invention claimed is:

1. A method of inhibiting proliferation of a mammalian cell at a site comprising contacting the mammalian cell with a nucleic acid encoding a mutant p27 protein having a mutation at a serine/threonine phosphorylation site at amino acid number ten that prevents or reduces phosphorylation by a serine/threonine kinase, wherein the nucleic acid is delivered locally to the site by a medical device.

2. The method of claim 1, wherein the mutant p27 protein retains its ability to arrest cells in the G1 phase.

3. The method of claim 1, wherein the mutant p27 protein comprises SEQ ID NO: 6.

4. The method of claim 1, wherein the nucleic acid comprises SEQ ID NO: 5.

5. The method of claim 1, wherein the nucleic acid is delivered by a device selected from the group consisting of a catheter, a needle injection device, a needleless injection device, a stent, a vascular graft, a stent graft and a coated vaso-occlusive device.

6. The method of claim 5, wherein the catheter is selected from the group consisting of an injection catheter, a balloon catheter, a double balloon catheter, a porous or microporous balloon catheter, a channel balloon catheter, a hydrogel-coated balloon catheter, an infusion catheter or a perfusion catheter.

7. The method of claim 5, wherein the stent is a coated stent or a bifurcated stent.

8. The method of claim 7, wherein the coated stent comprises the nucleic acid impregnated in a polymer.

9. The method of claim 1, wherein the nucleic acid is in an expression vector.

10. The method of claim 1, wherein the nucleic acid is combined with a liposome.

11. The method of claim 1, wherein the mutant p27 protein comprises a serine to alanine mutation at amino acid number ten.

12. The method of claim 1, wherein the serine/threonine kinase is KIS.

13. The method of claim 9, wherein the expression vector is a plasmid.

14. The method of claim 9, wherein the expression vector is a viral vector.

15. The method of claim 14, wherein the viral vector is an adenoviral vector.

16. The method of claim 1, wherein the mammalian cell is a human cell.

17. The method of claim 1, wherein the mammalian cell is a neointimal cell.

* * * * *

SEQUENCE LISTING

<160> NUMBER OF SEQ ID NOS: 15

<210> SEQ ID NO 1
<211> LENGTH: 1260
<212> TYPE: DNA
<213> ORGANISM: Homo sapiens
<220> FEATURE:
<221> NAME/KEY: CDS
<222> LOCATION: (1)..(1257)

<400> SEQUENCE: 1

```
atg gcg gga tcc ggc tgc gcc tgg ggc gcg gag ccg ccg cgt ttt ctg      48
Met Ala Gly Ser Gly Cys Ala Trp Gly Ala Glu Pro Pro Arg Phe Leu
1               5                   10                  15 gag gcc ttc ggg cgg ctg tgg cag gta cag agc cgt ctg ggt agc ggc      96
Glu Ala Phe Gly Arg Leu Trp Gln Val Gln Ser Arg Leu Gly Ser Gly
            20                  25                  30 tcc tcc gcc tcg gtg tat cgg gtt cgc tgc tgc ggc aac cct ggc tcg     144
Ser Ser Ala Ser Val Tyr Arg Val Arg Cys Cys Gly Asn Pro Gly Ser
        35                  40                  45 ccc ccc ggc gcc ctc aag cag ttc ttg ccg cca gga acc acc ggg gct     192
Pro Pro Gly Ala Leu Lys Gln Phe Leu Pro Pro Gly Thr Thr Gly Ala
    50                  55                  60 gcg gcc tct gcc gcc gag tat ggt ttc cgc aaa gag agg gcg gcg ctg     240
Ala Ala Ser Ala Ala Glu Tyr Gly Phe Arg Lys Glu Arg Ala Ala Leu
65                  70                  75                  80 gaa cag ttg cag ggt cac aga aac atc gtg act ttg tat gga gtg ttt     288
Glu Gln Leu Gln Gly His Arg Asn Ile Val Thr Leu Tyr Gly Val Phe
                85                  90                  95 aca atc cac ttt tct cca aat gtg cca tca cgc tgt ctg ttg ctt gaa     336
Thr Ile His Phe Ser Pro Asn Val Pro Ser Arg Cys Leu Leu Leu Glu
            100                 105                 110 ctc ctg gat gtc agt gtt tcg gaa ttg ctc tta tat tcc agt cac cag     384
Leu Leu Asp Val Ser Val Ser Glu Leu Leu Leu Tyr Ser Ser His Gln
        115                 120                 125 ggt tgt tcc atg tgg atg ata cag cat tgc gcc cga gat gtt ttg gag     432
Gly Cys Ser Met Trp Met Ile Gln His Cys Ala Arg Asp Val Leu Glu
    130                 135                 140 gcc ctt gct ttt ctt cat cat gag ggc tat gtc cat gcg gac ctc aaa     480
Ala Leu Ala Phe Leu His His Glu Gly Tyr Val His Ala Asp Leu Lys
145                 150                 155                 160 cca cgt aac ata ttg tgg agt gca gag aat gaa tgt ttt aaa ctc att     528
Pro Arg Asn Ile Leu Trp Ser Ala Glu Asn Glu Cys Phe Lys Leu Ile
                165                 170                 175 gac ttt gga ctt agc ttc aaa gaa ggc aat cag gat gta aag tat att     576
Asp Phe Gly Leu Ser Phe Lys Glu Gly Asn Gln Asp Val Lys Tyr Ile
            180                 185                 190 cag aca gac ggg tat cgg gct cca gaa gca gaa ttg caa aat tgc ttg     624
Gln Thr Asp Gly Tyr Arg Ala Pro Glu Ala Glu Leu Gln Asn Cys Leu
        195                 200                 205
```

-continued

```
gcc cag gct ggc ctg cag agt gat aca gaa tgt acc tca gct gtt gat    672
Ala Gln Ala Gly Leu Gln Ser Asp Thr Glu Cys Thr Ser Ala Val Asp
    210                 215                 220 ctg tgg agc cta gga atc att tta ctg gaa atg ttc tca gga atg aaa    720
Leu Trp Ser Leu Gly Ile Ile Leu Leu Glu Met Phe Ser Gly Met Lys
225                 230                 235                 240 ctg aaa cat aca gtc aga tct cag gaa tgg aag gca aac agt tct gct    768
Leu Lys His Thr Val Arg Ser Gln Glu Trp Lys Ala Asn Ser Ser Ala
                245                 250                 255 att att gat cac ata ttt gcc agt aaa gca gtg gtg aat gcc gca att    816
Ile Ile Asp His Ile Phe Ala Ser Lys Ala Val Val Asn Ala Ala Ile
            260                 265                 270 cca gcc tat cac cta aga gac ctt atc aaa agc atg ctt cat gat gat    864
Pro Ala Tyr His Leu Arg Asp Leu Ile Lys Ser Met Leu His Asp Asp
        275                 280                 285 cca agc aga aga att cct gct gaa atg gca ttg tgc agc cca ttc ttt    912
Pro Ser Arg Arg Ile Pro Ala Glu Met Ala Leu Cys Ser Pro Phe Phe
    290                 295                 300 agc att cct ttt gcc cct cat att gaa gat ctg gtc atg ctt ccc act    960
Ser Ile Pro Phe Ala Pro His Ile Glu Asp Leu Val Met Leu Pro Thr
305                 310                 315                 320 cca gtg cta aga ctg ctg aat gtg ctg gat gat gat tat ctt ggg aat    1008
Pro Val Leu Arg Leu Leu Asn Val Leu Asp Asp Asp Tyr Leu Gly Asn
                325                 330                 335 gaa gag gaa tat gaa gat gtt gta gaa gat gta aaa gag gag tgt caa    1056
Glu Glu Glu Tyr Glu Asp Val Val Glu Asp Val Lys Glu Glu Cys Gln
            340                 345                 350 aaa tat gga cca gtg gta tct cta ctt gtt cca aag gaa aat cct ggc    1104
Lys Tyr Gly Pro Val Val Ser Leu Leu Val Pro Lys Glu Asn Pro Gly
        355                 360                 365 aga gga caa gtc ttt gtt gag tat gca aat gct ggt gat tcc aaa gct    1152
Arg Gly Gln Val Phe Val Glu Tyr Ala Asn Ala Gly Asp Ser Lys Ala
    370                 375                 380 gcg cag aaa tta ctg act gga agg atg ttt gat ggg aag ttt gtt gtg    1200
Ala Gln Lys Leu Leu Thr Gly Arg Met Phe Asp Gly Lys Phe Val Val
385                 390                 395                 400 gct aca ttc tac ccg ctg agt gcc tac aag agg gga tat ctg tat caa    1248
Ala Thr Phe Tyr Pro Leu Ser Ala Tyr Lys Arg Gly Tyr Leu Tyr Gln
                405                 410                 415 acc ttg ctt taa                                                    1260
Thr Leu Leu <210> SEQ ID NO 2
<211> LENGTH: 419
<212> TYPE: PRT
<213> ORGANISM: Homo sapiens

<400> SEQUENCE: 2

Met Ala Gly Ser Gly Cys Ala Trp Gly Ala Glu Pro Pro Arg Phe Leu
1               5                   10                  15

Glu Ala Phe Gly Arg Leu Trp Gln Val Gln Ser Arg Leu Gly Ser Gly
            20                  25                  30

Ser Ser Ala Ser Val Tyr Arg Val Arg Cys Cys Gly Asn Pro Gly Ser
        35                  40                  45

Pro Pro Gly Ala Leu Lys Gln Phe Leu Pro Pro Gly Thr Thr Gly Ala
    50                  55                  60

Ala Ala Ser Ala Ala Glu Tyr Gly Phe Arg Lys Glu Arg Ala Ala Leu
65                  70                  75                  80

Glu Gln Leu Gln Gly His Arg Asn Ile Val Thr Leu Tyr Gly Val Phe
```

```
                            85                   90                      95
Thr Ile His Phe Ser Pro Asn Val Pro Ser Arg Cys Leu Leu Glu
                100                     105                 110
Leu Leu Asp Val Ser Val Ser Glu Leu Leu Tyr Ser Ser His Gln
            115                     120                 125
Gly Cys Ser Met Trp Met Ile Gln His Cys Ala Arg Asp Val Leu Glu
    130                     135                 140
Ala Leu Ala Phe Leu His His Glu Gly Tyr Val His Ala Asp Leu Lys
145                     150                 155                 160
Pro Arg Asn Ile Leu Trp Ser Ala Glu Asn Glu Cys Phe Lys Leu Ile
                    165                 170                 175
Asp Phe Gly Leu Ser Phe Lys Glu Gly Asn Gln Asp Val Lys Tyr Ile
                180                     185                 190
Gln Thr Asp Gly Tyr Arg Ala Pro Glu Ala Glu Leu Gln Asn Cys Leu
            195                     200                 205
Ala Gln Ala Gly Leu Gln Ser Asp Thr Glu Cys Thr Ser Ala Val Asp
    210                     215                 220
Leu Trp Ser Leu Gly Ile Ile Leu Leu Glu Met Phe Ser Gly Met Lys
225                     230                 235                 240
Leu Lys His Thr Val Arg Ser Gln Glu Trp Lys Ala Asn Ser Ser Ala
                    245                 250                 255
Ile Ile Asp His Ile Phe Ala Ser Lys Ala Val Val Asn Ala Ala Ile
                260                     265                 270
Pro Ala Tyr His Leu Arg Asp Leu Ile Lys Ser Met Leu His Asp Asp
            275                     280                 285
Pro Ser Arg Arg Ile Pro Ala Glu Met Ala Leu Cys Ser Pro Phe Phe
    290                     295                 300
Ser Ile Pro Phe Ala Pro His Ile Glu Asp Leu Val Met Leu Pro Thr
305                     310                 315                 320
Pro Val Leu Arg Leu Leu Asn Val Leu Asp Asp Tyr Leu Gly Asn
                    325                 330                 335
Glu Glu Glu Tyr Glu Asp Val Val Glu Asp Val Lys Glu Glu Cys Gln
                340                     345                 350
Lys Tyr Gly Pro Val Val Ser Leu Leu Val Pro Lys Glu Asn Pro Gly
            355                     360                 365
Arg Gly Gln Val Phe Val Glu Tyr Ala Asn Ala Gly Asp Ser Lys Ala
    370                     375                 380
Ala Gln Lys Leu Leu Thr Gly Arg Met Phe Asp Gly Lys Phe Val Val
385                     390                 395                 400
Ala Thr Phe Tyr Pro Leu Ser Ala Tyr Lys Arg Gly Tyr Leu Tyr Gln
                    405                 410                 415
Thr Leu Leu

<210> SEQ ID NO 3
<211> LENGTH: 1260
<212> TYPE: DNA
<213> ORGANISM: Artificial Sequence
<220> FEATURE:
<223> OTHER INFORMATION: Description of Artificial Sequence: hKIS mutant
      K54R
<220> FEATURE:
<221> NAME/KEY: CDS
<222> LOCATION: (1)..(1257)

<400> SEQUENCE: 3 atg gcg gga tcc ggc tgc gcc tgg ggc gcg gag ccg ccg cgt ttt ctg        48
```

```
            Met Ala Gly Ser Gly Cys Ala Trp Gly Ala Glu Pro Pro Arg Phe Leu
            1               5                   10                  15 gag gcc ttc ggg cgg ctg tgg cag gta cag agc cgt ctg ggt agc ggc        96
Glu Ala Phe Gly Arg Leu Trp Gln Val Gln Ser Arg Leu Gly Ser Gly
                20                  25                  30 tcc tcc gcc tcg gtg tat cgg gtt cgc tgc tgc ggc aac cct ggc tcg      144
Ser Ser Ala Ser Val Tyr Arg Val Arg Cys Cys Gly Asn Pro Gly Ser
            35                  40                  45 ccc ccc ggc gcc ctc agg cag ttc ttg ccg cca gga acc acc ggg gct      192
Pro Pro Gly Ala Leu Arg Gln Phe Leu Pro Pro Gly Thr Thr Gly Ala
50                  55                  60 gcg gcc tct gcc gcc gag tat ggt ttc cgc aaa gag agg gcg gcg ctg      240
Ala Ala Ser Ala Ala Glu Tyr Gly Phe Arg Lys Glu Arg Ala Ala Leu
65                  70                  75                  80 gaa cag ttg cag ggt cac aga aac atc gtg act ttg tat gga gtg ttt      288
Glu Gln Leu Gln Gly His Arg Asn Ile Val Thr Leu Tyr Gly Val Phe
                85                  90                  95 aca atc cac ttt tct cca aat gtg cca tca cgc tgt ctg ttg ctt gaa      336
Thr Ile His Phe Ser Pro Asn Val Pro Ser Arg Cys Leu Leu Leu Glu
            100                 105                 110 ctc ctg gat gtc agt gtt tcg gaa ttg ctc tta tat tcc agt cac cag      384
Leu Leu Asp Val Ser Val Ser Glu Leu Leu Leu Tyr Ser Ser His Gln
            115                 120                 125 ggt tgt tcc atg tgg atg ata cag cat tgc gcc cga gat gtt ttg gag      432
Gly Cys Ser Met Trp Met Ile Gln His Cys Ala Arg Asp Val Leu Glu
130                 135                 140 gcc ctt gct ttt ctt cat cat gag ggc tat gtc cat gcg gac ctc aaa      480
Ala Leu Ala Phe Leu His His Glu Gly Tyr Val His Ala Asp Leu Lys
145                 150                 155                 160 cca cgt aac ata ttg tgg agt gca gag aat gaa tgt ttt aaa ctc att      528
Pro Arg Asn Ile Leu Trp Ser Ala Glu Asn Glu Cys Phe Lys Leu Ile
                165                 170                 175 gac ttt gga ctt agc ttc aaa gaa ggc aat cag gat gta aag tat att      576
Asp Phe Gly Leu Ser Phe Lys Glu Gly Asn Gln Asp Val Lys Tyr Ile
            180                 185                 190 cag aca gac ggg tat cgg gct cca gaa gca gaa ttg caa aat tgc ttg      624
Gln Thr Asp Gly Tyr Arg Ala Pro Glu Ala Glu Leu Gln Asn Cys Leu
            195                 200                 205 gcc cag gct ggc ctg cag agt gat aca gaa tgt acc tca gct gtt gat      672
Ala Gln Ala Gly Leu Gln Ser Asp Thr Glu Cys Thr Ser Ala Val Asp
210                 215                 220 ctg tgg agc cta gga atc att tta ctg gaa atg ttc tca gga atg aaa      720
Leu Trp Ser Leu Gly Ile Ile Leu Leu Glu Met Phe Ser Gly Met Lys
225                 230                 235                 240 ctg aaa cat aca gtc aga tct cag gaa tgg aag gca aac agt tct gct      768
Leu Lys His Thr Val Arg Ser Gln Glu Trp Lys Ala Asn Ser Ser Ala
                245                 250                 255 att att gat cac ata ttt gcc agt aaa gca gtg gtg aat gcc gca att      816
Ile Ile Asp His Ile Phe Ala Ser Lys Ala Val Val Asn Ala Ala Ile
            260                 265                 270 cca gcc tat cac cta aga gac ctt atc aaa agc atg ctt cat gat gat      864
Pro Ala Tyr His Leu Arg Asp Leu Ile Lys Ser Met Leu His Asp Asp
            275                 280                 285 cca agc aga aga att cct gct gaa atg gca ttg tgc agc cca ttc ttt      912
Pro Ser Arg Arg Ile Pro Ala Glu Met Ala Leu Cys Ser Pro Phe Phe
290                 295                 300 agc att cct ttt gcc cct cat att gaa gat ctg gtc atg ctt ccc act      960
Ser Ile Pro Phe Ala Pro His Ile Glu Asp Leu Val Met Leu Pro Thr
305                 310                 315                 320
```

```
cca gtg cta aga ctg ctg aat gtg ctg gat gat gat tat ctt ggg aat      1008
Pro Val Leu Arg Leu Leu Asn Val Leu Asp Asp Asp Tyr Leu Gly Asn
            325                 330                 335 gaa gag gaa tat gaa gat gtt gta gaa gat gta aaa gag gag tgt caa      1056
Glu Glu Glu Tyr Glu Asp Val Val Glu Asp Val Lys Glu Glu Cys Gln
        340                 345                 350 aaa tat gga cca gtg gta tct cta ctt gtt cca aag gaa aat cct ggc      1104
Lys Tyr Gly Pro Val Val Ser Leu Leu Val Pro Lys Glu Asn Pro Gly
    355                 360                 365 aga gga caa gtc ttt gtt gag tat gca aat gct ggt gat tcc aaa gct      1152
Arg Gly Gln Val Phe Val Glu Tyr Ala Asn Ala Gly Asp Ser Lys Ala
370                 375                 380 gcg cag aaa tta ctg act gga agg atg ttt gat ggg aag ttt gtt gtg      1200
Ala Gln Lys Leu Leu Thr Gly Arg Met Phe Asp Gly Lys Phe Val Val
385                 390                 395                 400 gct aca ttc tac ccg ctg agt gcc tac aag agg gga tat ctg tat caa      1248
Ala Thr Phe Tyr Pro Leu Ser Ala Tyr Lys Arg Gly Tyr Leu Tyr Gln
                405                 410                 415 acc ttg ctt taa                                                       1260
Thr Leu Leu <210> SEQ ID NO 4
<211> LENGTH: 419
<212> TYPE: PRT
<213> ORGANISM: Artificial Sequence
<220> FEATURE:
<223> OTHER INFORMATION: Description of Artificial Sequence: hKIS mutant
      K54R

<400> SEQUENCE: 4

Met Ala Gly Ser Gly Cys Ala Trp Gly Ala Glu Pro Pro Arg Phe Leu
 1               5                  10                  15

Glu Ala Phe Gly Arg Leu Trp Gln Val Gln Ser Arg Leu Gly Ser Gly
             20                  25                  30

Ser Ser Ala Ser Val Tyr Arg Val Arg Cys Cys Gly Asn Pro Gly Ser
         35                  40                  45

Pro Pro Gly Ala Leu Arg Gln Phe Leu Pro Pro Gly Thr Thr Gly Ala
     50                  55                  60

Ala Ala Ser Ala Ala Glu Tyr Gly Phe Arg Lys Glu Arg Ala Ala Leu
 65                  70                  75                  80

Glu Gln Leu Gln Gly His Arg Asn Ile Val Thr Leu Tyr Gly Val Phe
                 85                  90                  95

Thr Ile His Phe Ser Pro Asn Val Pro Ser Arg Cys Leu Leu Leu Glu
            100                 105                 110

Leu Leu Asp Val Ser Val Ser Glu Leu Leu Tyr Ser Ser His Gln
        115                 120                 125

Gly Cys Ser Met Trp Met Ile Gln His Cys Ala Arg Asp Val Leu Glu
    130                 135                 140

Ala Leu Ala Phe Leu His His Glu Gly Tyr Val His Ala Asp Leu Lys
145                 150                 155                 160

Pro Arg Asn Ile Leu Trp Ser Ala Glu Asn Glu Cys Phe Lys Leu Ile
                165                 170                 175

Asp Phe Gly Leu Ser Phe Lys Glu Gly Asn Gln Asp Val Lys Tyr Ile
            180                 185                 190

Gln Thr Asp Gly Tyr Arg Ala Pro Glu Ala Glu Leu Gln Asn Cys Leu
        195                 200                 205

Ala Gln Ala Gly Leu Gln Ser Asp Thr Glu Cys Thr Ser Ala Val Asp
    210                 215                 220
```

```
Leu Trp Ser Leu Gly Ile Ile Leu Glu Met Phe Ser Gly Met Lys
225                 230                 235                 240

Leu Lys His Thr Val Arg Ser Gln Glu Trp Lys Ala Asn Ser Ser Ala
                245                 250                 255

Ile Ile Asp His Ile Phe Ala Ser Lys Ala Val Asn Ala Ala Ile
            260                 265                 270

Pro Ala Tyr His Leu Arg Asp Leu Ile Lys Ser Met Leu His Asp Asp
                275                 280                 285

Pro Ser Arg Arg Ile Pro Ala Glu Met Ala Leu Cys Ser Pro Phe Phe
            290                 295                 300

Ser Ile Pro Phe Ala Pro His Ile Glu Asp Leu Val Met Leu Pro Thr
305                 310                 315                 320

Pro Val Leu Arg Leu Leu Asn Val Leu Asp Asp Tyr Leu Gly Asn
                325                 330                 335

Glu Glu Glu Tyr Glu Asp Val Val Glu Asp Val Lys Glu Glu Cys Gln
                340                 345                 350

Lys Tyr Gly Pro Val Val Ser Leu Leu Val Pro Lys Glu Asn Pro Gly
                355                 360                 365

Arg Gly Gln Val Phe Val Glu Tyr Ala Asn Ala Gly Asp Ser Lys Ala
            370                 375                 380

Ala Gln Lys Leu Leu Thr Gly Arg Met Phe Asp Gly Lys Phe Val Val
385                 390                 395                 400

Ala Thr Phe Tyr Pro Leu Ser Ala Tyr Lys Arg Gly Tyr Leu Tyr Gln
                405                 410                 415

Thr Leu Leu

<210> SEQ ID NO 5
<211> LENGTH: 597
<212> TYPE: DNA
<213> ORGANISM: Artificial Sequence
<220> FEATURE:
<223> OTHER INFORMATION: Description of Artificial Sequence: 27 Mutant
      S10A

<400> SEQUENCE: 5
atgtcaaacg tgcgagtgtc taacggggct cctagcctgg agcggatgga cgccaggcag      60
gcggagcacc ccaagccctc ggcctgcagg aacctcttcg gcccggtgga ccacgaagag     120
ttaacccggg acttggagaa gcactgcaga gacatggaag aggcgagcca gcgcaagtgg     180
aatttcgatt ttcagaatca caaaccccta gagggcaagt acgagtggca agaggtggag     240
aagggcagct tgcccgagtt ctactacaga ccccgcggc ccccaaagg tgcctgcaag      300 gtgccggcgc aggagagcca ggatgtcagc gggagccgcc cggcggcgcc tttaattggg     360
gctccggcta actctgagga cacgcatttg gtggacccaa agactgatcc gtcggacagc     420
cagacggggt tagcggagca atgcgcagga ataaggaagc gacctgcaac cgacgattct     480
tctactcaaa acaaaagagc caacagaaca gaagaaaatg tttcagacgg ttccccaaat     540
gccggttctg tggagcagac gcccaagaag cctggcctca agacgtca aacgtaa       597

<210> SEQ ID NO 6
<211> LENGTH: 198
<212> TYPE: PRT
<213> ORGANISM: Artificial Sequence
<220> FEATURE:
<223> OTHER INFORMATION: Description of Artificial Sequence: p27 Mutant
      S10A
```

-continued

<400> SEQUENCE: 6

Met Ser Asn Val Arg Val Ser Asn Gly Ala Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: p27KIP1CR5P
      primer

<400> SEQUENCE: 7
cgtgaattca tgtcaaacgt gcgagtg                                           27

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: p27KIP1CR3P
      primer

<400> SEQUENCE: 8
cgtggatcct tacgtctggc gtcgaaggcc                                        30

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
      p27KIP1NH23P primer

<400> SEQUENCE: 9
ctgggatcct gtagaactcg ggcaagct                                          28

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
     p27KIP1CIIH5P primer

<400> SEQUENCE: 10
ctggaattct tagcggagca gtgtcca                                    27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: p575P
     primer

<400> SEQUENCE: 11
cgtgaattca tggaacgctt ggcctcc                                    27

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: p573P
     primer

<400> SEQUENCE: 12
cgtggatcct caagagtctg caaacgcgc                                  29

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: p215P
     primer

<400> SEQUENCE: 13
cgtgaattcg gcaccatgtc caatcct                                    27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: p213P
     primer

<400> SEQUENCE: 14
ctggtcgacg tgggcacttc agggttt                                    27

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence:
     p27KIP1NH3S10M5P primer

<400> SEQUENCE: 15
gctggatcca tgtcaaacgt gagagtgtcc aacgctccga g                    41